United States Patent [19]

Nalewajek et al.

[11] Patent Number: 5,856,286
[45] Date of Patent: Jan. 5, 1999

[54] SURFACTANTS FOR USE IN DRYING AND DRY CLEANING COMPOSITIONS

[75] Inventors: David Nalewajek, West Seneca; Leonard Michael Stachura, Hamburg; Gary John Zyhowski, Lancaster, all of N.Y.

[73] Assignee: AlliedSignal Inc., Morristown, N.J.

[21] Appl. No.: 881,179

[22] Filed: Jun. 23, 1997

[51] Int. Cl.$^6$ ....................................................... C11D 3/28
[52] U.S. Cl. .............................. 510/288; 134/4; 510/500; 546/346; 546/347
[58] Field of Search ..................................... 510/285, 500, 510/288; 134/4; 546/346, 347

[56] References Cited

U.S. PATENT DOCUMENTS

| | | | |
|---|---|---|---|
| 2,727,923 | 12/1955 | Husted | 260/567.6 |
| 3,257,407 | 6/1966 | Brace | 260/290 |
| 4,062,849 | 12/1977 | Foulletier et al. | 260/279 R |
| 4,401,584 | 8/1983 | Tajkowski et al. | 252/194 |
| 4,438,026 | 3/1984 | Tajkowski | 252/545 |
| 4,836,281 | 6/1989 | Robin et al. | 166/272 |

FOREIGN PATENT DOCUMENTS

| | | |
|---|---|---|
| 2040601 A1 | 10/1991 | Canada . |
| 06-208248 | 7/1994 | Japan . |
| 1 269 095 | 5/1968 | United Kingdom . |

OTHER PUBLICATIONS

Journal of Physical Chemistry (abstract) 1989, vol. 2, pp. 377–382, May 1989.

*Primary Examiner*—Paul Lieberman
*Assistant Examiner*—John R. Hardee
*Attorney, Agent, or Firm*—Colleen D. Szuch; Jay P. Friedenson

[57] ABSTRACT

The invention provides a fluorinated surfactant for use with halocarbon and hydrofluoroether solvents. Additionally, the invention provides drying, dry cleaning, and soil repellency compositions containing a halocarbon or hydrofluoroether and a fluorinated surfactant.

27 Claims, No Drawings

SURFACTANTS FOR USE IN DRYING AND DRY CLEANING COMPOSITIONS

FIELD OF THE INVENTION

The invention relates to surfactants useful with halocarbon and hydrofluoroethers solvents. In particular, the surfactants of the invention may be used with halocarbons, including hydrochlorofluorocarbons and hydrofluorocarbons, and hydrofluoroethers.

BACKGROUND OF THE INVENTION

The use of aqueous compositions for the surface treatment of metal, ceramic, glass, and plastic articles is well known. Additionally, cleaning, plating, and deposition of coatings on the surface of articles is known to be carried out in aqueous media. In both cases, a halocarbon solvent and a hydrophobic surfactant may be used to displace water from a water-laden surface.

A variety of solvent-surfactant drying compositions for water displacement are utilized. For example, solvent-surfactant compositions based on 1,1,2-trichlorotrifluoroethane ("CFC-113") are used. However, toxicity and environmental concerns are leading to a decline in the use of such CFC-based systems.

The identification of suitable surfactants for use with hydrochlorofluorocarbons ("HCFC's"), hydrofluorocarbons ("HFC's"), and hydrofluoroethers ("HFE's") solvents suitable to replace CFC solvents is proving difficult for a variety of reasons. First, many of the known surfactants cannot be dissolved in such solvents. Further, dry cleaning, drying, and water displacement require surfactants that impart distinct properties to the solvent used. For the removal of oil from machined parts, the surfactant must aid in the removal of the soils that would otherwise only be sparingly soluble in such solvents. Additionally, water displacement requires a surfactant that does not form a stable emulsion with water. Therefore, one must not only identify those surfactants soluble in the HCFC, HFC, or HFE solvent selected, but surfactants that also have the desired activity in the solvents.

The present invention provides a new class of HCFC, HFC, and HFE soluble, hydrophobic, fluorine-containing surfactants. These surfactants exhibit desirable surface activity in the solvents and are useful in displacing water.

DESCRIPTION OF THE INVENTION AND PREFERRED EMBODIMENTS

It is a discovery of the invention that the placement of fluorine on the surfactant molecule is critical to surfactant solubility in HCFC, HFC, and HFE solvents as well as the maintenance of the surface activity and hydrophobicity of the surfactant. Thus, in one embodiment, the invention comprises a surfactant selected from:

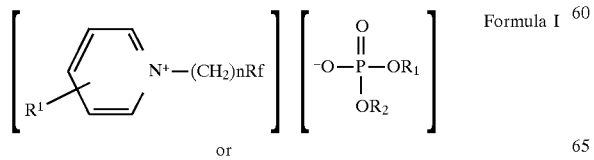

Formula I or

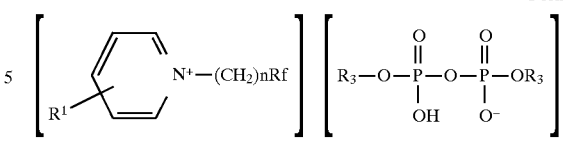

Formula II wherein R' is hydrogen, $C_1$–$C_5$ alkyl, aryl, alkylaryl, $C_1$–$C_5$ fluoroalkyl, fluoroaryl, or fluoroalkylaryl, $R_1$, $R_2$, and $R_3$ may be the same or different and are hydrogen, linear or branched $C_1$ to $C_{16}$ alkyl, fluoroalkyl, aryl or alkylaryl, or

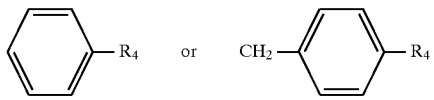

wherein $R_4$ is a linear or branched $C_1$ to $C_{16}$ alkyl or fluoroalkyl group, provided that not more than one of the $R_1$, $R_2$, and $R_3$ groups is hydrogen, n=$_1$ to 16, and Rf is $C_mF_{2m+1}$ wherein m=2, 4, 6, 8, 10 or 12, or mixtures of such surfactant compositions. Preferably, n=2, 3 or 4. More preferably, n=2 and Rf is alphafluoropolydifluoromethylene with an average m value of 6–8. Especially preferred heteroaromatic surfactants are the oligomeric perfluoroalkylpyridinium salts of 4-tert-octylphenyl-mono- and or di-acid phosphates. It is a discovery of the invention that for surfactants in which the placement of the fluorinated component is on the hetero atom, i e., the nitrogen of the pyridine ring, the surfactant will exhibit drying activity In another embodiment, the invention provides a composition comprising a solvent comprising a halocarbon, a hydrofluoroether, or mixtures thereof and a surfactant of the above formulae wherein the components are present in amounts sufficient to provide effective drying or dry cleaning. The solvent-surfactant compositions of the invention effectively displace water from a broad range of substrates including, without limitation: metals, such as stainless steel, aluminum alloys, and brass; glass and ceramic surfaces, such as glass, borosilicate glass and unglazed alumina; silica, such as silicon wafers; fired alumina; and the like. Further, the compositions of the invention either do not form noticeable emulsions with the displaced water or form only insignificant amounts of such emulsions.

In still another embodiment, the invention provides solvent-surfactant compositions useful in, and their use in, processes for treating fabric to impart soil repellency. The compositions comprise a solvent comprising a halocarbon, a hydrofluoroether, or mixtures thereof and a surfactant of the above formulae wherein the components are present in amounts sufficient to provide effective soil repellency. These compositions promote soil removal and, when present in a rinse stage, impart soil repellency.

The preferred embodiment of the fluorine-containing surfactant of the invention may be prepared according to the following scheme. Other compounds within the surfactant class may be prepared analogously For the surfactants not specifically shown, modifications to this scheme for their manufacture will be readily apparent to one ordinarily skilled in the art.

Step 1:

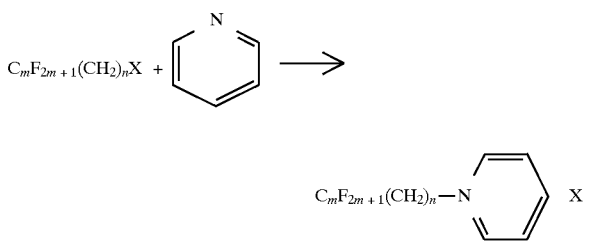

wherein X is a halogen and Rf, m and n are as defined above.

Step 2:

octylphenol + P$_2$O$_5$ ⟶ octylphenyl acid phosphate

Step 3:

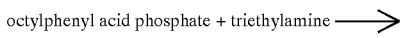

octylphenyl acid phosphate + triethylamine ⟶ triethylamine salt of octylphenyl acid phosphate

Step 4:

Cation exchange of the tertiary fluorinated heteroaromatic product of Step 1 for the triethylamine of the octylphenyl acid phosphate product of Step 3 ⟶

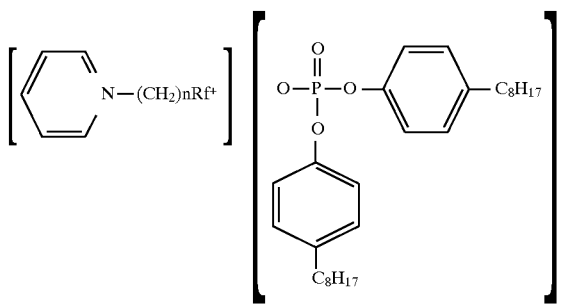

By halocarbon is meant any hydrohalocarbon, including without limitation hydrochlorocarbon or hydrobromocarbon, hydrochlorocarbon, chlorofluorocarbon, HCFC, or HFC capable of dissolving the surfactant. More specifically, useful halocarbons may be any linear or branched halocarbon, or a halocarbon containing a hetero atom, including without limitation oxygen, nitrogen, or sulfur Suitable linear or branched halocarbons are those of the formula $C_xZ_{2x+2}$, wherein x is 2 to 36 and Z may be hydrogen, bromine, chlorine, tiluorine, and combinations thereof such that the total number of halogen and hydrogen atoms does not exceed the value of 2x+2.

Preferably, the halocarbon component comprises at least one volatile halocarbon. For purposes of this invention, by "volatile halocarbon" is meant a halocarbon having a boiling point of at least about 10° C. at atmospheric pressure. Preferred volatile halocarbons are halocarbons with a boiling point of at least about 15° C. at atmospheric pressure. Particularly preferred volatile halocarbons are hydrofluorocarbons including, without limitation, isomers of pentafluoropropane, isomers of hexafluorobutane, pentafluorobutane, octafluoropentane, heptafluoropentane, and heptafluorobutane. Particularly preferred HCFC halocarbons include isomers of dichlorofluoroethane, dichlorotrifluoroethane, and mixtures thereof. Also particularly preferred are mixtures of at least two of an HFC, HCFC, or at least one HFC and at least one HCFC.

Many HFC's and HCFC's are commercially available and others may be prepared according to methods known in the art. For example, HFC-356mcfq is currently not commercially available, but may be prepared according to the method disclosed in U.S. Pat. No. 5,610,128, which reference is incorporated herein in its entirety.

Suitable HFE's are linear and branched aliphatic aromatic, or cyclic HFE's of the general formula $C_xF_{2x+1}OC_mH_{2m+1}$ wherein x is at least 2 to 16 and m is at least 1 to 16. Illustrative HFE's include, without limitation 1,1,1,2,3,3-pentafluoropropylmethyl ether, isomers of hydrofluorocarbon ethers of hexafluorobutane and HFE-7100 which is an isomeric mixture of methyl nonafluorobutylether and methyl nonafluoroisobutylether, and HFE-71DE which is a mixture of HFE-7100 and 1,2-trans-dichloroethylene. Preferably, the HFE is HFE-7100 or HFE-71DE. Additionally, the HFE may be a blend of at least one HFE and a CFC, HCFC, or HFC.

The solvent primarily functions to reduce the amount of water on the surface of the article to be dried. The surfactant functions primarily to assist in cleaning the article and to displace any remaining water from the surface of the article. The amounts of halocarbon and surfactant used may vary widely depending on the application, but are readily apparent to those skilled in the art. U.S. Pat. Nos. 4,438,026 and 4,401,584, incorporated herein in their entireties, disclose the proportions in which such materials may be combined.

The amount of solvent used is an amount sufficient to transfer the surfactant to the article. By effective amount of surfactant is meant an amount that is capable of improving the drying, dry cleaning, or soil repellency capability of the halocarbon to any extent. Preferably, the amount of surfactant used will be no greater than about 5 weight percent of the total weight of the solvent-surfactant composition. However, although uneconomical, large amounts may be used if after treatment with the composition, the article being dried is treated with a volatile halocarbon having either no or a small amount of surfactant. More preferably, the amount of surfactant is about 0.005 to about 3.0, still more preferably about 0.005 to about 0.5, most preferably about 0.05 to about 0.3, weight percent. In a preferred embodiment for drying applications, the amount of surfactant is at least about 0.005 weight percent, more preferably about 0.005 to about 0.5, most preferably about 0.01 to about 0.2, weight percent. In a preferred embodiment for dry cleaning applications, about 0.005 to about 3.0, more preferably about 0.01 to about 0.5 weight percent is used.

The compositions of the invention may be used to clean and/or dry nonabsorbent substrates and articles constructed of such materials as metals, glasses, ceramics, and the like. Thus, in yet another embodiment, the invention provides a method for drying the surface of a substrate comprising the steps of contacting the substrate with a composition comprising a solvent comprising a halocarbon, a hydrofluoroether, or mixtures thereof and effective amounts of a surfactant of the Formula (I) or (II) and then removing the solvent-surfactant composition from the article.

The invention also provides a method for dry cleaning an article which comprises the steps of contacting, or exposing, the article to a composition comprising a solvent comprising a halocarbon, a hydrofluoroether, or mixtures thereof and effective amounts of a surfactant of the Formula (I) or (II) above and then removing the solvent-surfactant composition from the article.

The invention additionally provides a method for imparting soil repellency to a fabric comprising the steps of contacting, or exposing, the fabric to a composition comprising a solvent comprising a halocarbon, a hydrofluoroether, or mixtures thereof and an effective amount of a surfactant of the Formulae (I) or (II) and removing the solvent from the fabric.

The manner of contacting is not critical and may vary widely. For example, the article may be immersed in a container of the composition or the article may be sprayed with the composition. Complete immersion of the article is preferred because it ensures contact between all exposed surfaces of the article and the composition. Any method that can provide such contact may be used. Typically, the contacting time is up to about 10 minutes, but this time is not critical and longer times may be used if desired. In the preferred embodiment of the invention, the contacting time is from about 5 seconds to about 240 seconds. Among the preferred embodiments, most preferred are those in which contacting time is from about 5 seconds to about 180 seconds.

The contacting temperature may also vary widely depending on the boiling point of the compositions. In general, the temperature is equal to or less than about such boiling point. Following the contacting step, the article is removed from contact with the composition and removal of composition adhering to exposed surfaces of the article is effected by any conventional means such as evaporation. Optionally, the remaining minimal amounts of surfactant adhering to the article may be removed further by contacting the article with surfactant free solvent that is hot or cold. Finally, holding the article in the solvent vapor will decrease further the presence of the surfactant residue remaining on the article. Again, removal of solvent adhering to the article is effected by evaporation.

In general, removal, or evaporation, of the composition is effected in less than about 30 seconds, preferably less than about 10 seconds. Neither temperature nor pressure is critical. Atmospheric or subatmospheric pressure may be employed and temperatures above and below the boiling point of the halocarbon may be used. Optionally, additional surfactants may be included in the overall composition as desired.

Also optionally, a co-solvent may be included such as, without limitation, an alcohol, ester, or ketone. Preferably, the co-solvent does not extract appreciably into the water. Also preferably a second halocarbon may be used as a co-solvent. When a co-solvent is used, the co-solvent is present in amounts of from about 1 to about 50 weight percent, preferably from about 4 to about 45 percent, based on the total composition.

In yet another embodiment, a substrate is provided with a coating of the surfactant of the invention in an amount effective to provide the fabric with soil repellent characteristics. This may be accomplished by dissolving the surfactant in a suitable solvent, preferably one of the above-enumerated. The substrate is then wetted with the composition by spraying or immersion for a length of time sufficient to cause the composition to be imbibed by the substrate. Moreover, the surfactant, preferably in a solution of a halocarbon, may enhance the removal of solids from the substrate by contacting the soiled substrate with the solvent-surfactant compositions. This method will find its greatest utility in cases in which the substrate is a fabric.

The compositions and processes of the invention are preferably carried out or used with conventional drying or dry cleaning machines and systems. Illustrative of such drying machines are those described in U.S. Pat. No. 3,386,181, which is hereby incorporated in its entirety by reference.

The invention will be clarified further by a consideration of the following, nonlimiting examples.

EXAMPLES

Example 1

The following preparation is a modification of the procedure disclosed in United Kingdom Patent No. 1,269,095, incorporated in its entirety herein by reference. Into a 2 L reaction flask was added an excess of pyridine (992 g, 12.5 mol). The organic was heated to 80° C. followed by the drop-wise addition of 720 g, 1.3 mol, Zonyl-TELB-1, a perfluoroalkyl iodide telomer. After the addition was completed, the reaction contents were heated at 80° C. for an additional 2 hours. The reaction mass was cooled to 0° C., effecting precipitation of the product which was then filtered and air dried to yield 577 g, 73% yield of yellow, perfluoroalkyl pyridinium telomer iodide salt.

Example 2

To a 5 L flask was added 225.7 g octylphenyl acid phosphate neutralized with triethylamine. 3300 g of CFC-113 were added and the mixture heated to reflux. 338.14 g of the intermediate prepared in Example 1 was added to the refluxing mixture. After three hours, the reaction was cooled to ambient temperature and 3 L water were added. The resulting organic layer was phase separated and the solvent removed under 100 mm vacuum to yield 504 g product.

Example 3

For purposes of evaluating the performance of the solvent-surfactant composition of the invention in the displacement of water, 35 mL of the solvent containing 500 ppm by weight of the surfactant prepared in Example 2 were placed in a 100 mL beaker fitted with a cooling coil. The solution was brought to a boil, the coiling coil confining the solvent vapor to the beaker. Duplicate 316 stainless steel coupons, wet-abraded to a water-break-free condition, were immersed in water and then into the boiling sample solution. The time required to displace the water from the coupon was recorded, a minimum observation time of 5 second being chosen.

After an initial observation of drying performance, 35 mL of water were added to the boiling solution. The solution was kept boiling for 5 minutes in order to provide contact between the solution and the water. The mixture was then transferred to a separatory funnel and the time for phase separation was noted. Rapid separation into clear phases with no emulsion layer is an indication that the solution will perform successfully in the application. A clear water phase indicates that no gross loss of drying solvent to the water effluent of a commercial machine would be expected. In this test, a clear solvent phase indicates the ability of the drying solvent to expel displaced water from a drying machine in a particle time frame, i.e., water will not accumulate in the solvent phase.

The water washing was performed a total of 4 times with subsequent determination of the drying time, that is the time required to displace water from the test coupons, after each water washing. It is known from experience with commercial drying sloevents that after the life test, the final drying time should be no longer than one minute. Final drying times much in excess of 1 minute indicate that the life bath of the drying solvent will be inadequate in commercial applications. Table 1 provides the initial drying performance, phase separation behavior, and performance as a function of water throughput for various solvents and sufactants.

TABLE 1

|  | Initial Drying Time (sec) | Phase Separation Time (sec) | Clarity Top Phase | Clarity Bottom Phase | Dry Time After Wash 1 | Dry Time After Wash 2 | Dry Time After Wash 3 | Dry Time After Wash 4 |
|---|---|---|---|---|---|---|---|---|
| HCFC-141B | 30 | 30 | Yes | Yes | 30 | 35 | 40 | 45 |
| HFE-7100 | 10 | 30 | Yes | Yes | 10 | 10 | 10 | 15 |
| CFC-113 | 5 | 10 | Yes | Yes | 5 | 5 | 10 | 10 |
| HFC-245EA | 5 | 5 | Yes | No | 5 | 5 | 15 | 25 |
| HFC-356MCFQ | 5 | 5 | Yes | Yes | 5 | 5 | 5 | 5 |
| HFE-71DE | 5 | 5 | Yes | Yes | 5 | 10 | 10 | 15 |
| HFC-4310 | 5 | 45 | No | Yes | 5 | 15 | 60 | 60 |
| 1-H-perfluoroheptane | 5 | 5 | Yes | Yes | 5 | 5 | 5 | 5 |
| HCFC-225CB | 5 | 5 | Yes | Yes | 5 | 5 | 15 | 25 |
| HCFC-123 | 5 | 10 | Yes | Yes | 5 | 5 | 5 | 5 |

The results demonstrate that the octylphenyl acid phosphate salt of perfluoroalkyl prydinium telomer perfoms as an active surfactant for water displacement with respect to drying time, phase separation, phase clarity, and in a wide range of halocarbon solvents at the 500 ppm level.

Example 4

A variety of commercial surfactants were evaluated in select halocarbon solvents and their efficacy in drying was determined. The results are listed on Table 2.

TABLE 2

| Surfactant | HFC-245ea | HFC-356mcfq | Perfluoromethyl-morpholine |
|---|---|---|---|
| 3M FC-120 (anionic) | insoluble | insoluble | insoluble |
| 3M FC-135 (cationic) | soluble; no drying activity | insoluble | insoluble |
| 3M FC-171 (fluorinated alkylpolyoxyethylene) | soluble; no drying activity | soluble; no drying activity | not determined |
| 3M FC-431 (fluorinated alkylalkoxylate) | soluble; no drying activity | 60 sec. dry | not determined |
| 3M FC-740 (fluorinated alkyl ester) | insoluble | insoluble | not determined |
| 3M Perfluoroaliphatic amidoalkanol | 30 sec. dry | soluble; no drying acitivity | 30 sec. dry |
| Air Products Dabco DC193 (polyalkylsiloxane) | not run | 60 sec. dry | not determined |
| Du Pint Zonyl FSO-100 (fluorinated nonionic polymeric ethyleneoxide) | soluble; no drying activity | soluble; no drying activity | not determined |
| OSI Silwet L-7500 (polyalkylene oxide modified polydimethylsiloxane) | not determined | insoluble | not determined |
| Witco Emphos CS-131 (polyoxyalkylated alkyl aryl; phosphate ester) | not determined | insoluble | not determined |
| Witco Witconol NP-15 (polyoxy-1,2-ethanediylalpha-nonphenyl omega hydroxy) | not determined | sl. soluble; no drying activity | not determined |
| Du Pont Zonyl IRP (telomer B phosphate diethanol amine salt) | not determined | insoluble | not determined |
| Rhone-Poulenc Rhodaquat DAET-90 (complex ditallow quarternary sulfate) | not determined | insoluble | not determined |
| Albright & Wilson Amgard ND (dimelamine phosphate) | not determined | insoluble | not determined |
| Albright & Wilson Amgard MC (ammonium poly phosphate) | not determined | insoluble | not determined |
| Ethox Chemicals, Inc. CAM2 (polyoxyethylene coconut amine) | not determined | insoluble | not determined |

TABLE 2-continued

| Surfactant | HFC-245ea | HFC-356mcfq | Perfluoromethyl-morpholine |
|---|---|---|---|
| Tomah Products ES-2 (dihydroxyethyl soya amine) | not determined | insoluble | not determined |

The results demonstrate that there is no obvious correspondence between surfactant-solvent systems and drying activity. Drying solvent compositions are not limited to the use of one surfactant. Surfactants can be used in combination. Also, certain surfactants known to be useful in water displacement may be either insoluble or only sparingly soluble in HFC's or HCFC's. The incorporation of a co-solvent that is soluble in the HFC and renders the surfactant soluble in the combined solvent matrix was found to be a useful means to employ surfactants that are essentially insoluble in HFC's alone. The co-solvent preferably forms an azeotrope with the HFC. If the co-solvent does not form an azeotrope with the HFC, it must be higher boiling than the HFC in order to remain with the surfactant in the boiling chamber of a commercial drying machine. It also is useful to select a co-solvent that is essentially insoluble in water so that the co-solvent is not carried out of the drying machine with the effluent water. Water-soluble co-solvents may be used, but require replenishing.

Example 5

A co-solvent was used to solubilize a hydrophobic surfactant in an HFC. The results are shown on Table 3. Drying was tested as described in Example 3 as the initial drying performance.

TABLE 3

| Composition | Drying Time (secs) |
|---|---|
| HFC-245ea/500 ppm DRS* | insoluble |
| HFC-245ea/500 ppm DRS/5 wt % trichloroethylene | 30 |
| HFC-245ea/1000 ppm DRS/5 wt % trichloroethylene | 10 |
| HFC-245ea/1000 ppm DRS/10 wt % trichloroethylene | 5 |

*DRS is the surfactant found in the Allied Signal Inc.'s Genosolv DRSC drying solvent, a product using CFC-113 as the solvent.

Example 6

Dry cleaning solvent performance may be enhanced by adding a surfactant that prevents redeposition of soil during the cleaning process. Likewise, surfactants may be added to the cleaning solvent that impart water and/or soil repellency. Placement of water or oil droplets on the surface of woven cotton fabric and observation of the rate of absorption indicates the level of repellency. Table 4 illustrates the oil repellency of the surfactant of the invention from HFC-356mcfq.

For the experiment, a 2"×2" cloth swatch was first immersed in HFC solvent containing the surfactants. The cloth was then removed and allowed to air dry. Next, and oil droplet was deposited on the surface of the swatch. The time required for the oil droplet to absorb into the sloth was noted. The longer times are indicative of greater oil repellency.

TABLE 4

|  | Surfactant 0 ppm | Surfactant 500 ppm | Surfactant 5000 ppm |
|---|---|---|---|
| 20W Motor Oil Trial 1 | 21 sec | 105 sec | 225 sec |
| 20W Motor Oil Trial 2 | 20 sec | 99 sec | 210 sec |

Example 7

Clean 2"×2" cotton fabric swatches were analyzed for initial brightness and color using a Milton Roy Color-Mate color analyzer available from Milton Roy Co., Rochester N.Y. The instrument was set to white tile standard. The difference from the standard was reported. A drop of oil was placed on the cloth and the time required for the drop to absorb noted. An additional nine drops were deposited on the swatch and the swatches were dried overnight. Color and brightness readings were again taken. The soiled swatches were then placed in vials containing solvent or a solvent-surfactant composition. The vials were shaken for 3 minutes and the swatches removed and allowed to air dry. Color and brightness were again measured. Finally, an oil droplet was placed on the swatch to determine absorption time, a measure of repellency. Color and brightness readings as well as oil absorption times are shown on Table 5 for HFC-365mcf with 3.9 wt percent isopropanol and surfactant The color and brightness readings of the washed swatches were in between the values measured for initial, clean swatches and the values for the fully soiled swatches. The optimum cleaning cycle was not derived. The measurements were made according to the Hunter Color Space system with the letter "a" denoting redness (a positive value) to greenness (a negative value), "b" denoting yellowness (a positive value) to blueness (a negative value). The lightness variable "L" ranges from 0 (black) to 100 (white). Tri-stimulus values "X", "Y", and "Z" allow a mathematical representation of color based on the trichromacy of vision. For matching color evaluations, two stimuli produce the same color if each of the tri-stimulus values are equal for the two respective stimuli.

TABLE 5

| Oil | Color/Brightness Category | Initial | Soiled | Cleaned | Percent recovery | Oil Absorption Time |
|---|---|---|---|---|---|---|
| 5000 ppm | L | −4.83 | −35.5 | −16.2 | 63.1 | 90 sec |
| Surfactant; | a | 0.09 | 39.5 | 15.5 | 61 | 90 sec |
| Bowman's | b | −1.9 | 1.9 | −2.05 | — | 90 sec |

TABLE 5-continued

| Oil | Color/Brightness Category | Initial | Soiled | Cleaned | Percent recovery | Oil Absorption Time |
|---|---|---|---|---|---|---|
| Thread Sealant | X | −8.3 | −38.3 | −19.5 | 63.6 | 90 sec |
|  | Y | −8.8 | −53.5 | −27.5 | 58.1 | 90 sec |
|  | Z | −6.5 | −57.5 | −26.5 | 61.3 | 90 sec |
|  | dE | 5.2 | 53.0 | 22.5 | 64.0 | 90 sec |
| 0 ppm | L | −4.5 | −36.8 | −18.3 | 57.5 | — |
| Surfactant; | a | −0.01 | 41.3 | 18.0 | 56.3 | — |
| Bowman's | b | −1.9 | 2.5 | −2.16 | — | — |
| Thread Sealant | X | −7.8 | −39.4 | −21.6 | 56.2 | — |
|  | Y | −8.2 | −54.9 | −30.6 | 52.0 | — |
|  | Z | −5.8 | −59.6 | −29.5 | 56.1 | — |
|  | dE | 4.9 | 55.4 | 25.8 | 58.7 | — |
| 50000 ppm | L | −4.5 | −14.9 | −10.1 | 46.1 | 2 min |
| Surfactant; | a | 0.04 | −7.03 | −6.3 | 10.8 | 2 min |
| Hocut 763 | b | −2.0 | 4.4 | 3.2 | — | 2 min |
|  | X | −7.7 | −27.2 | −19.8 | 38.3 | 2 min |
|  | Y | −8.1 | −25.5 | −17.8 | 44.4 | 2 min |
|  | Z | −5.6 | −32.2 | −22.9 | 35.0 | 2 min |
|  | dE | 4.9 | 17.1 | 12.3 | 39.0 | 2 min |
| 0 ppm | L | −4.5 | −14.7 | −10.6 | −40.5 | — |
| Surfactant; | a | 0.01 | −8.6 | −7.6 | 11.7 | — |
| Hocut 763 | b | −1.9 | 3.19 | 1.99 | — | — |
|  | X | −7.7 | −27.6 | −21.0 | 33.0 | — |
|  | Y | −8.2 | −25.2 | −18.5 | 39.0 | — |
|  | Z | −5.7 | −30.4 | −22.0 | 33.8 | — |
|  | dE | 4.9 | 17.3 | 13.0 | 33.5 | — |

The results on Table 5 demonstrate that the swatches contacted with surfactant during the cleaning process were as a result more resistant to oil absorption as noted by increased oil times. The percent recovery comparing soiled with cleaned swatches to initial swatch condition is greater in virtually every category in the case in which surfactant was present. A sample of cloth changed in hue and brightness when it was dirtied and then cleaned. The percent recovery is a measure of the effectiveness of the cleaning composition in returning the sample back to its initial color value.

Table 6 shows the results of similar tests for a similar composition without the isopropanol co-solvent. Oil repellency was not measured.

TABLE 6

| Oil | Color/Brightness Category | Initial | Soiled | Cleaned | Percent recovery |
|---|---|---|---|---|---|
| 5000 ppm | L | −4.7 | −39.1 | −23.5 | 45.2 |
| Surfactant; | a | 0.01 | 43.1 | 25.9 | 39.8 |
| Bowman's | b | −1.9 | 3.5 | −1.8 | — |
| Thread Sealant | X | −8.1 | −41.7 | −26.4 | 45.6 |
|  | Y | −8.5 | −57.5 | −38.3 | 39.2 |
|  | Z | −6.2 | −63.0 | −38.0 | 40.3 |
|  | dE | 5.1 | 58.3 | 35.1 | 43.6 |
| 0 ppm | L | −4.6 | −36.8 | −23.7 | 40.9 |
| Surfactant; | a | 0.04 | 41.0 | 25.5 | 37.9 |
| Bowman's | b | −2.2 | 2.3 | −2.5 | — |
| Thread Sealant | X | −8.0 | −39.4 | −26.7 | 40.4 |
|  | Y | −8.4 | −54.9 | −38.4 | 35.5 |
|  | Z | −5.9 | −59.5 | −37.4 | 41.4 |
|  | dE | 5.1 | 55.2 | 34.9 | 40.5 |
| 5000 ppm | l | −4.6 | −14.9 | −11.5 | 33.0 |
| Surfactant; | a | 0.02 | −6.6 | −5.6 | 15.8 |
| HOCUT 763 | b | −1.9 | 4.9 | 3.9 | 14.5 |
|  | X | −7.8 | −27.0 | −21.5 | 28.8 |
|  | Y | −8.26 | −25.5 | −20.0 | 31.6 |
|  | Z | −5.9 | −32.9 | −26.2 | 25.0 |
|  | dE | 4.9 | 17.0 | 13.3 | 30.5 |
| 0 ppm | L | −4.5 | −15.5 | −13.7 | 16.9 |
| Surfactant; | a | 0.07 | −7.1 | −7.2 | 2.0 |

TABLE 6-continued

| Oil | Color/Brightness Category | Initial | Soiled | Cleaned | Percent recovery |
|---|---|---|---|---|---|
| Hocut 763 | b | −2.1 | 5.2 | 4.8 | 6.1 |
|  | X | −7.8 | −28.1 | −25.2 | 14.4 |
|  | Y | −8.2 | −26.5 | −23.6 | 16.0 |
|  | Z | −5.6 | −34.2 | −30.8 | 12.1 |
|  | dE | 4.9 | 17.8 | 16.2 | 13.0 |

The results show that in percent recovery comparing soiled with clean swatches to initial swatch condition, there is enhanced cleaning with surfactant-solvent compositions compared with solvent alone.

What is claimed is:

1. A surfactant of the formula:

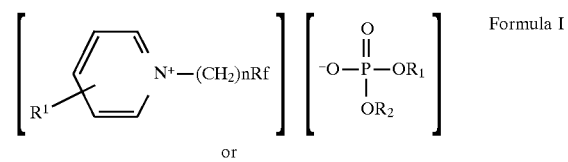

Formula I

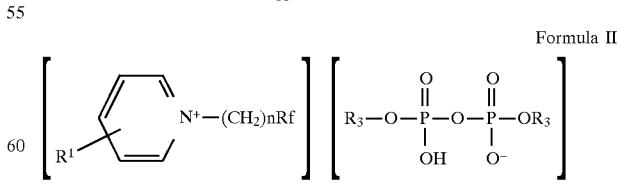

Formula II wherein R' is hydrogen, $C_1$–$C_5$ alkyl, aryl, alkylaryl, $C_1$–$C_5$ fluoroalkyl, fluoroaryl, or fluoroalkylaryl, $R_1$, $R_2$, and $R_3$ are the same or different and are hydrogen, linear or branched $C_1$ to $C_{16}$ alkyl, fluoroalkyl, aryl or alkylaryl, or

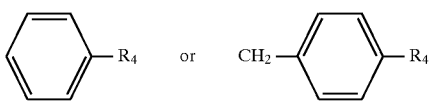

wherein $R_4$ is a linear or branched $C_1$ to $C_{16}$ alkyl or fluoroalkyl group, provided that the anion is organic, that not more than one of the $R_1$, $R_2$, and $R_3$ groups is hydrogen, n=1 to 16, and Rf is $C_mF_{2m+1}$ wherein m=2, 4, 6, 8, 10 or 12, and mixtures thereof.

2. The surfactant of claim 1 wherein n=2, 3 or 4.

3. The surfactant of claim 1 wherein n=2 and Rf is alphafluoropolydifluoromethylene with an average m value of 6–8.

4. The surfactant of claim 1 wherein the surfactant is an oligomeric perfluoroalkylpyridinium salt of 4-tert-octylphenyl-monoacid phosphates, an oligomeric perfluoroalkylpyridinium salt of 4-tert-octylphenyl-diacid phosphates, or mixtures thereof.

5. A composition comprising a solvent comprising a halocarbon, a hydrofluoroether, or mixtures thereof and an effective amount of a surfactant of the formula:

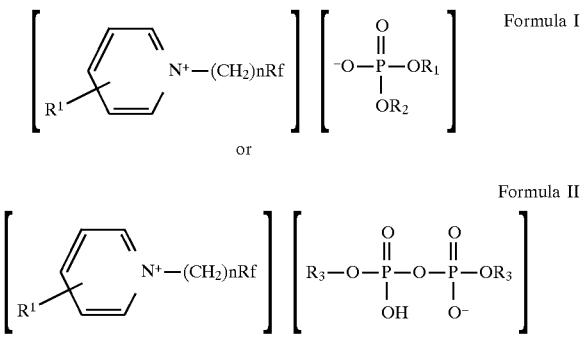

wherein R' is hydrogen, $C_1$–$C_5$ alkyl, aryl, alkylaryl, $C_1$–$C_5$ fluoroalkyl, fluoroaryl, fluoroalkylaryl, $R_1$, $R_2$, and $R_3$ are the same or different and are hydrogen, linear or branched $C_1$ to $C_{16}$ alkyl, fluoroalkyl, aryl or alkylaryl, or

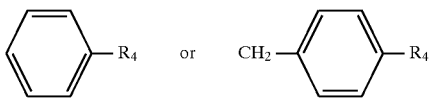

wherein $R_4$ is a linear or branched $C_1$ to $C_{16}$ alkyl or fluoroalkyl group, provided that the anion is organic, that not more than one of the $R_1$, $R_2$, and $R_3$ groups is hydrogen, n=1 to 16, and Rf is $C_mF_{2m+1}$ wherein m=2, 4, 6, 8, 10 or 12, or mixtures thereof.

6. The composition of claim 5 wherein in=2, 3 or 4.

7. The composition of claim 5 wherein n=2 and Rf is alphafluoropolydifluoromethylene with an average m value of 6–8.

8. The composition of claim 5 wherein the surfactant is an oligomeric perfluoroalkylpyridinium salt of 4-tert-octylphenyl-monoacid phosphates, an oligomeric perfluoroalkylpyridinium salt of 4-tert-octylphenyl-diacid phosphates, or mixtures thereof.

9. The compositions of claims 5, 6, 7, or 8 wherein the halocarbon is a linear halocarbon, a branched halocarbon, a halocarbon containing a heteroatom that is oxygen, nitrogen, or sulfur, or mixtures thereof.

10. The compositions of claim 9 wherein the halocarbon is of the formula $C_xZ_{2x+2}$, wherein x is 2 to 36 and Z may be hydrogen, bromine, chlorine, fluorine, and combinations thereof and the hydrofluoroether is of the formula $C_xF_{2x+1}OC_mH_{2m+1}$ wherein x is at least 2 to 16 and m is at least 1 to 16.

11. The composition of claim 9 wherein the halocarbon is an isomer of pentafluoropropane, an isomer of hexafluorobutane, an isomer of pentafluorobutane, an isomer of octafluoropentane, an isomer of heptafluoropentane, an isomer of heptafluorobutane, an isomer of dichlorofluoroethane, an isomer of dichlorotrifluoroethane, or mixtures thereof.

12. The composition of claim 11 wherein the hydrofluoroether is 1,1,1,2,3,3-pentafluoropropylmethyl ether, isomers of hydrofluorocarbon ethers of hexafluorobutane, an isomeric mixture of methyl nonafluorobutylether and methyl nonafluoroisobutylether, an isomeric mixture of methyl nonafluorobutylether and methyl nonafluoroisobutylether and 1,2-trans-dichloroethylene, or mixtures thereof.

13. The composition of claim 9 wherein the halocarbon is 1,1-dichloro-1-fluoroethane.

14. The composition of claim 9 wherein the halocarbon is 2,2-dichloro-1,1,1-trifluoroethane.

15. The composition of claims 12 wherein the halocarbon is 1,1-dichloro-1-fluoroethane.

16. The composition of claim 12 wherein the halocarbon is 2,2-dichloro-1,1,1-trifluoroethane.

17. The compositions of claims 5, 6, 7, or 8 wherein the hydrofluoroether is a linear hydrofluoroether, a branched hydrofluoroether, or a cyclic hydrofluoroether and wherein the hydrofluoroethers are of the formula $C_xF_{2x+1}OC_mH_{2m+1}$ wherein x is at least 2 to 16 and m is at least 1 to 16.

18. The compositions of claims 17 wherein the hydrofluoroether is 1,1,1,2,3,3-pentafluoropropylmethyl ether, isomers of hydrofluorocarbon ethers of hexafluorobutane, an isomeric mixture of methyl nonafluorobutylether and methyl nonafluoroisobutylether, an isomeric mixture of methyl nonafluorobutylether and methyl nonafluoroisobutylether and 1,2-trans-dichloroethylene, or mixtures thereof.

19. The composition of claim 17 wherein the hydrofluoroether is an isomeric mixture of methyl nonafluorobutylether and methyl nonafluoroisobutylether.

20. The composition of claim 17 wherein the hydrofluoroether is an isomeric mixture of methyl nonafluorobutylether and methyl nonafluoroisobutylether and 1,2-trans-dichloroethylene.

21. The composition of claim 19 wherein the halocarbon is 1,1-dichloro-1-fluoroethane.

22. The composition of claim 20 wherein the halocarbon is 1,1-dichloro-1-fluoroethane.

23. The composition of claim 19 wherein the halocarbon is 2,2-dichloro-1,1,1-trifluoroethane.

24. The composition of claim 20 wherein the halocarbon is 2,2-dichloro-1,1,1-trifluoroethane.

25. A method for drying a surface of a substrate comprising the steps of contacting the substrate with the composition of claim 5; and removing the composition from the substrate.

26. A method for dry cleaning comprising the steps of contacting the substrate with the composition of claim 5; and removing the composition from the substrate.

27. A method for imparting soil repellency to a fabric comprising the steps of contacting the fabric with the composition of claim 5; and removing the solvent from the fabric.

* * * * *